United States Patent
Tao et al.

(10) Patent No.: US 11,549,924 B2
(45) Date of Patent: Jan. 10, 2023

(54) METHANE SENSOR AUTOMATIC BASELINE CALIBRATION

(71) Applicant: Baker Hughes Oilfield Operations LLC, Houston, TX (US)

(72) Inventors: Chong Tao, San Diego, CA (US); Gary S. Parece, Billerica, MA (US); Anthony Kowal, Berlin, MA (US); Jon W. Chow, Billerica, MA (US); Ashraf El-Messidi, Nashville, TN (US)

(73) Assignee: Baker Hughes Oilfield Operations LLC, Houston, TX (US)

( * ) Notice: Subject to any disclaimer, the term of this patent is extended or adjusted under 35 U.S.C. 154(b) by 284 days.

(21) Appl. No.: 17/062,029

(22) Filed: Oct. 2, 2020

(65) Prior Publication Data
US 2022/0107295 A1    Apr. 7, 2022

(51) Int. Cl.
*G01N 33/00* (2006.01)
*G01K 13/00* (2021.01)

(52) U.S. Cl.
CPC ......... *G01N 33/0006* (2013.01); *G01K 13/00* (2013.01)

(58) Field of Classification Search
CPC ... G01N 2201/127; G01N 2201/12746; G01N 33/0006; G01K 13/00
See application file for complete search history.

(56) References Cited

U.S. PATENT DOCUMENTS

2020/0244742 A1* 7/2020 Henshaw ............... G16Y 20/10
2020/0256839 A1* 8/2020 Ghadiali ............. G01N 33/004

OTHER PUBLICATIONS

Fuglsang et al., "Continuous methane concentration measurements at the Greenland ice sheet-atmosphere interface using a low-cost, low-power metal oxide sensor system" Jun. 22, 2020, Copernicus Publications/European Geosciences Union. pp. 3319-3328 (Atmos. Meas. Tech., 13, 3319-3328, 2020) (Year: 2020).*

* cited by examiner

*Primary Examiner* — Herbert K Roberts
*Assistant Examiner* — Anthony W Megna Fuentes
(74) *Attorney, Agent, or Firm* — Mintz Levin Cohn Ferris Glovsky and Popeo, PC; Lisa Adams

(57) ABSTRACT

A method for baseline calibration of methane sensor includes receiving data characterizing methane detection by a sensor and sensor measurement parameters. The received data characterizing methane detection includes a plurality of methane measurements and detection times associated with the plurality of methane measurements. The method also includes determining a first plurality of calibrated methane measurements by at least calibrating the plurality of methane measurement based on the sensor measurement parameters and one or more of a humidity and a temperature associated with the sensor. The method further includes calculating an offset parameter based on a difference between a global baseline reference and one of a previous baseline value and a measurement baseline value associated with the first plurality of calibrated methane measurements. The method also includes providing a second plurality of calibrated methane measurements by at least subtracting the offset parameter from the first plurality of calibrated methane measurements.

18 Claims, 3 Drawing Sheets

METHANE SENSOR AUTOMATIC BASELINE CALIBRATION

BACKGROUND

Sensors can be deployed in a variety of environments for sensing contaminants and concentration of particles that need to be tracked in the environment. Some sensors (e.g., methane sensor) can be placed around gas well pads to detect gas (e.g., methane) leaks. Data corresponding to detection by the sensor can be transmitted to a controller that can process the data, determine the concentration of contamination and generate notification if the concentration of the contamination exceeds desired levels.

SUMMARY

Various aspects of the disclosed subject matter may provide one or more of the following capabilities.

In one implementation, a method for baseline calibration of methane sensor includes receiving data characterizing methane detection by a sensor and sensor measurement parameters. The received data characterizing methane detection includes a plurality of methane measurements and detection times associated with the plurality of methane measurements. The method also includes determining a first plurality of calibrated methane measurements by at least calibrating the plurality of methane measurement based on the sensor measurement parameters and one or more of a humidity and a temperature associated with the sensor. The method further includes calculating an offset parameter based on a difference between a global baseline reference and one of a previous baseline value and a measurement baseline value associated with the first plurality of calibrated methane measurements. The method also includes providing a second plurality of calibrated methane measurements by at least subtracting the offset parameter from the first plurality of calibrated methane measurements.

One or more of the following features can be included in any feasible combination.

In one implementation, the method further includes determining the measurement baseline value. The determining includes selecting a subset of methane measurements from the first plurality of calibrated methane measurements. The values of the subset of methane measurements are below a predetermined percentile value and the measurement baseline value is a mean of the subset of methane measurements.

In one implementation, determining the offset parameter includes determining that the measurement baseline value is less than a threshold baseline value; and determining the offset parameter based on difference between the measurement baseline value and the global baseline reference. In another implementation, determining the offset parameter includes determining that the measurement baseline value is above a threshold baseline value; and determining the offset parameter based on difference between the previous baseline value and the global baseline reference. The sensor measurement parameters, the global baseline reference, the threshold baseline value and the previous baseline value are received from a database. In yet another implementation, the method further includes updating the previous baseline value in the database, the updating including setting the previous baseline value to the measurement baseline value.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

These and other capabilities of the disclosed subject matter will be more fully understood after a review of the following figures, detailed description, and claims.

BRIEF DESCRIPTION OF THE FIGURES

These and other features will be more readily understood from the following detailed description taken in conjunction with the accompanying drawings, in which.

DETAILED DESCRIPTION

The operation of a methane sensor (e.g., a metal-oxide methane sensor) configured to detect methane leaks or fugitive methane at industrial sites can be impacted by the environment of the methane sensor. For example, temperature and/or humidity of the industrial site can affect the methane measurement data generated by the methane sensor. Methane measurement data can be calibrated to account for changes in temperature and/or humidity of the industrial site. However, the aforementioned calibration may not compensate other variations in the methane measurement data (e.g., caused due to aging of the methane detector). These variations my lead to a drift in the baseline of the methane measurement by the methane detector (e.g., indicative of ambient methane levels in the atmosphere). Some implementations of the current subject matter provides for automatically calibrating the drift in the measured baseline of the methane sensor. This can be done by using the average global methane concentration in the atmosphere (e.g., 1.88 parts per million by volume, or PPMv) or a site specific known ambient methane concentration as a reference (sometimes referred to as "global baseline reference"), and calibrating the measurement data based on the offset between the measured baseline of the sensor and the global baseline reference of methane concentration.

Figure 1:
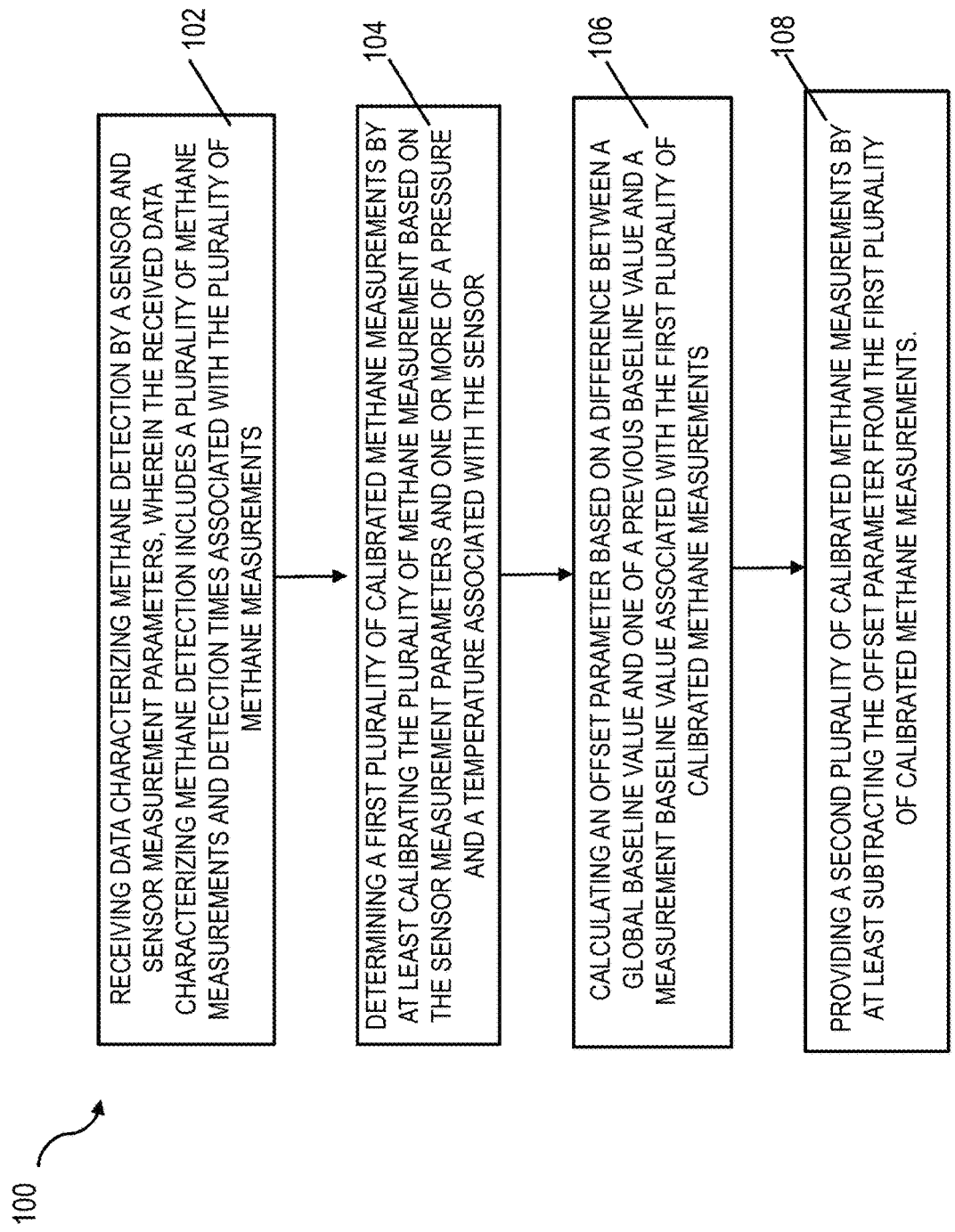
FIG. 1 illustrates a flowchart of an exemplary method for calibrating a methane sensor.
Figure 2:
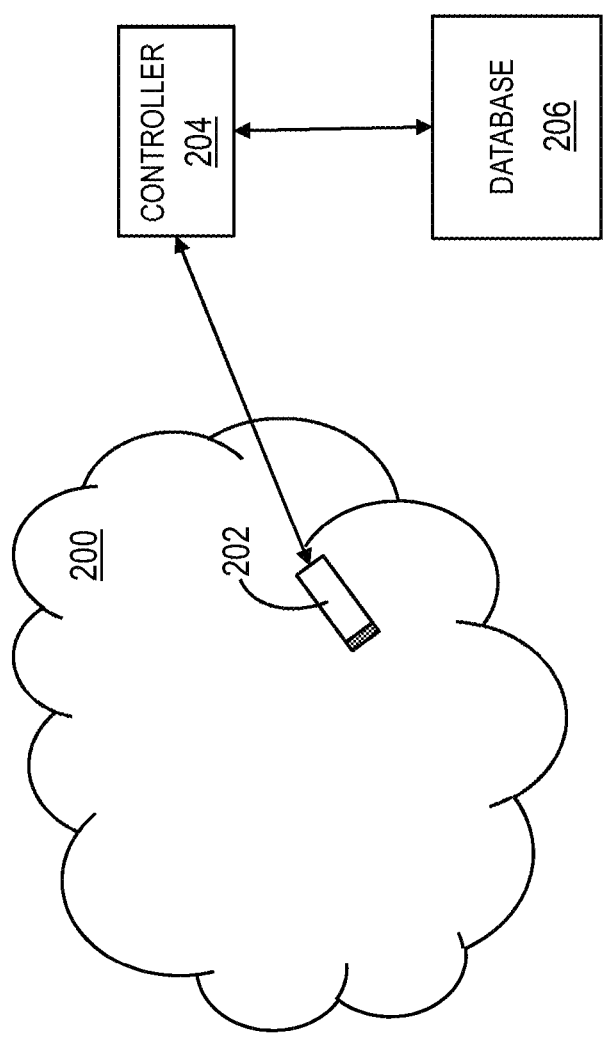
FIG. 2 illustrates an exemplary industrial site where methane leaks or fugitive methane can be inspected by a methane sensor.

FIG. 1 illustrates a flowchart of an exemplary method for calibrating a methane sensor. At step 102, data characterizing methane detection by a sensor and sensor calibration parameters is received. The received data characterizing methane detection includes a plurality of methane measurements and detection times associated with the plurality of methane measurements. For example, the plurality of methane measurements can include a methane measurement at each detection time. FIG. 2 illustrates an exemplary industrial site 200 that can be inspected by a methane sensor for a methane leak or fugitive methane monitoring. The industrial site 200 can include a detection system 202 that can include one or more sensors (e.g., methane sensor, temperature sensor, humidity sensor, etc.). The methane sensor in the detection system (not shown) can detect surrounding methane level (e.g., due to a methane leak in the industrial site).

Data characterizing the methane detection can be transmitted (e.g., periodically). For example, the methane sensor can be configured to activate periodically (e.g., once a few minutes, once an hour, once a day etc.) and perform methane detection over a detection time-period (e.g., a predetermined period). After each detection time-period (or a set of detection time periods), data characterizing methane detection can be transmitted that can be received by the controller 204. The controller 204 can also receive temperature and/or humidity measurements from the industrial site 200 (e.g., by temperature and/or humidity detector in the detection system 202).

The controller 204 can receive measurement parameters associated with the methane sensor in the detection system 202 that can allow for calibrating/calculating methane measurement data for various temperature, humidity and methane levels in the industrial site 200. It can be desirable to calibrate the measurement data from a methane sensor because the operation of the methane sensor can change based on environmental conditions. In some implementations, the measurement parameters can be stored in a database 206. Additionally or alternately, the measurement parameters can be provided by the methane sensor in the industrial site 200.

Returning to FIG. 1, at step 104, a first plurality of calibrated methane measurements can be determined by calibrating the methane measurement data from the methane sensor (e.g., methane sensor in detection system 202). The measurement parameters along with temperature and/or humidity measurements (e.g., by temperature/humidity sensors in the detection system 202) can be used to generate calibrated methane measurements ("first calibration"). In some implementations, the measurement parameters can be coefficients of a polynomial equation that can take temperature and/or humidity measurements values as inputs and generate a scaling factor based on which the methane measurement data from the methane sensor can be calibrated. As described above, calibrating the methane measurement data for temperature/humidity at the industrial may not be sufficient. For example, additional calibration may be needed to account for drift in the baseline methane measurement by the methane sensor (e.g., due to aging of the methane sensor).

The additional calibration ("second calibration") can be performed by determining a measurement baseline value associated with the calibrated methane measurements (e.g., generated after temperature and/or humidity calibration). Measurement baseline value can be determined by selecting a subset of the calibrated methane measurements. The subset of calibrated methane measurements can be determined by selecting a portion of the calibrated methane measurement that corresponds to a predetermined percentile value of the plurality of calibrated methane measurement (e.g., $20^{th}$ percentile, $25^{th}$ percentile, etc.). In other words, the calibrated methane measurement that constitute a predetermined percentile range of the calibrated methane measurement (e.g., bottom quartile, bottom quintile, etc.) are selected in the subset.

After the selection of the subset of calibrated methane measurements, the measurement baseline value can be a metric representative of the subset (e.g., mean/median of the subset of calibrated methane measurements). The measurement baseline value can be representative of atmospheric methane measurement by the methane sensor (e.g., after the methane leak at the industrial site 200 has dissipated and the methane sensor is detecting the atmospheric methane levels). It can be desirable that the measurement baseline value matches the average global methane concentration in the atmosphere or a known site-specific ambient methane level (global baseline reference). The value of the global baseline reference can be around 1.88 PPMv. A discrepancy between the measurement baseline value and the global baseline reference can indicate that further calibration of the methane sensor is needed.

In some implementations, the measurement baseline value can be greater than a threshold baseline value (e.g., 5 parts per million of methane by volume). This can be indicative of a persistent leak at the industrial site 200. In other words, the methane sensor is unable to detect the atmospheric methane without the influence of the methane leak at the industrial site 200. As a result, the measurement baseline value may not be indicative of atmospheric methane measurement or global baseline reference, and the measurement baseline value of a previous measurement of the methane sensor ("previous baseline value") may be a better indicator of the atmospheric methane measurement by the sensor. The threshold baseline value can be stored in a database 206 and can be received by the controller 204.

At step 106, an offset parameter for the second calibration can be calculated. In some implementations, the offset parameter can be the difference between the measurement baseline value and the global baseline reference (e.g., when the measurement baseline value is below the threshold baseline value). In some implementations, the offset parameters can be the difference between the previous baseline value and the global baseline reference (e.g., when the measurement baseline value is above the threshold baseline value).

Figure 3:
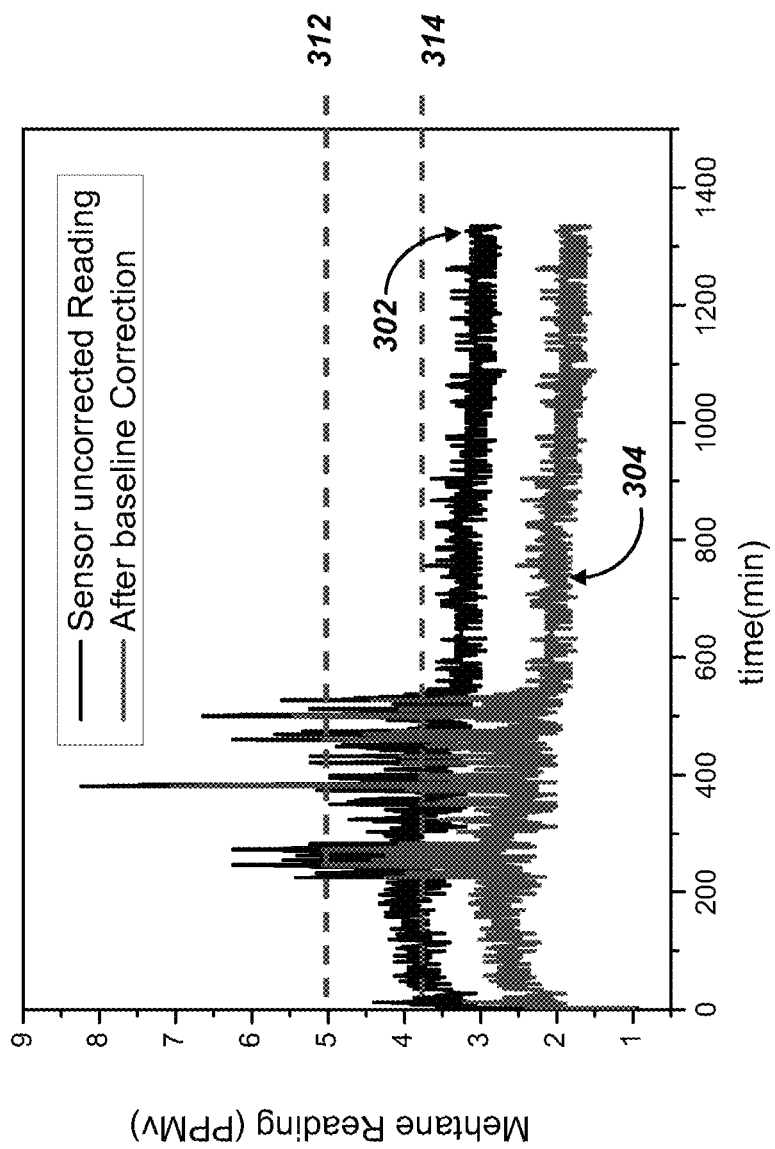
FIG. 3 illustrates exemplary plots of calibrated methane measurements.

At step 108, a second plurality of calibrated methane measurements can be provided (e.g., to the database 206, to a user via a graphical user interface (GUI) display device. This can be done by determining the second plurality of calibrated methane measurements subtracting the offset parameter from the calibrated methane measurement obtained from the first calibration. FIG. 3 illustrates exemplary plots of calibrated methane measurements (in parts per million by volume [PPMv] vs detection times [in minutes]). Plot 302 is the plot of the first plurality of calibrated methane measurements obtained after the first calibration (e.g., calibrating for temperature/humidity variations at the methane sensor). Plot 304 is the plot of the second plurality of calibrated methane measurement obtained after the second calibration (e.g., calibrating for deviations in measurement baseline value from global baseline reference by subtracting the offset value from the first plurality of calibrated methane measurement). Marker 312 indicates the predetermined threshold baseline value (e.g. 5 PPMv) and marker 314 indicates the measurement baseline value (e.g., the mean value of the bottom quartile of the first plurality of calibrated methane measurements in plot 302). The range of the subset of calibrated methane measurement values can be representative of a predetermined percentile range (e.g. bottom quartile, bottom quintile, etc.) of the first plurality of calibrated methane values.

As described above, the various parameters (e.g., sensor measurement parameters, the global baseline reference, the threshold baseline value and the previous baseline value, etc.) can be stored in a database (e.g., database 206). Prior to performing the calibration, the controller 204 can fetch one or more parameter values from the database 206. Additionally or alternately, if the measurement baseline value is used in the calculation of offset parameter (e.g., when the measurement baseline value is less than the threshold baseline value), the previous baseline value can be set to the measurement baseline value.

This approach can have several advantages. For example, the average global methane concentration has small variations (e.g., based on geographic location), and can be a stable and reliable reference (e.g., global baseline reference can be set to 1.88 PPMv). Automatically calibrating the drift in the measured baseline of the methane sensor using the average global methane concentration in the atmosphere or a site specific known ambient methane concentration as a reference, and calibrating the measurement data based on the offset between the measured baseline of the sensor and the global baseline reference of methane concentration can be cheap and efficient. For example, no additional sensors or data acquisition is needed. In some implementations, the methane sensors deployed at industrial sites do not have to be recalibrated (e.g. sent back to the factory for recalibration) resulting in reduction of downtime and/or costs. In some implementations, the computational cost for implementing this calibration can be small (e.g., calculation of offset may not be computationally intensive). Moreover, some implementations of this approach can greatly improve the accuracy of the sensors (e.g., for low methane concentration such as below 10 parts per million by volume).

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a Read-Only Memory or a Random Access Memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web interface through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

What is claimed is:

1. A computer-implemented method comprising:
   receiving, by one or more processors from a methane detection system comprising a sensor, data characterizing methane detection by the sensor and sensor measurement parameters, wherein the data characterizing methane detection comprises a plurality of methane measurements and detection times associated with the plurality of methane measurements; wherein the sensor is located at an industrial site;
   determining, by the one or more processors, a first plurality of calibrated methane measurements by at least calibrating the plurality of methane measurements based on the sensor measurement parameters and one or more of a humidity and a temperature associated with the sensor;
   calculating, by the one or more processors, an offset parameter based on a difference between a global baseline reference and one of a previous baseline value and a measurement baseline value associated with the first plurality of calibrated methane measurements; and
   providing, by the one or more processors, a second plurality of calibrated methane measurements by at least subtracting the offset parameter from the first plurality of calibrated methane measurements.

2. The computer-implemented method of claim 1, further comprising determining the measurement baseline value by:
   selecting a subset of calibrated methane measurements from the first plurality of calibrated methane measurements, wherein values of the subset of calibrated methane measurements are below a predetermined percentile value,
   wherein the measurement baseline value is a mean of the subset of calibrated methane measurements.

3. The computer-implemented method of claim 2, wherein determining the offset parameter comprises:
   determining that the measurement baseline value is less than a threshold baseline value; and
   determining the offset parameter based on the difference between the measurement baseline value and the global baseline reference.

4. The computer-implemented method according to claim 3, wherein the sensor measurement parameters, the global baseline reference, the threshold baseline value and the previous baseline value are received from a database.

5. The computer-implemented method of claim 4, further comprising updating the previous baseline value in the database by setting the previous baseline value to the measurement baseline value.

6. The computer-implemented method of claim 2, wherein determining the offset parameter comprises:
   determining that the measurement baseline value is above a threshold baseline value; and
   determining the offset parameter based on the difference between the previous baseline value and the global baseline reference.

7. A system comprising:
   at least one data processor;
   memory coupled to the at least one data processor, the memory storing instructions to cause the at least one data processor to perform operations comprising:
     receiving, from a methane detection system comprising a sensor, data characterizing methane detection by the sensor and sensor measurement parameters, wherein the data characterizing methane detection comprises a plurality of methane measurements and detection times associated with the plurality of methane measurements; wherein the sensor is located at an industrial site;
     determining a first plurality of calibrated methane measurements by at least calibrating the plurality of methane measurements based on the sensor measurement parameters and one or more of a humidity and a temperature associated with the sensor;
     calculating an offset parameter based on a difference between a global baseline reference and one of a previous baseline value and a measurement baseline value associated with the first plurality of calibrated methane measurements; and
     providing a second plurality of calibrated methane measurements by at least subtracting the offset parameter from the first plurality of calibrated methane measurements.

8. The system of claim 7, wherein the operations further include determining the measurement baseline value, the determining comprising:
   selecting a subset of calibrated methane measurements from the first plurality of calibrated methane measurements, wherein values of the subset of calibrated methane measurements are below a predetermined percentile value,
   wherein the measurement baseline value is a mean of the subset of calibrated methane measurements.

9. The system of claim 8, wherein determining the offset parameter comprises:
- determining that the measurement baseline value is less than a threshold baseline value; and
- determining the offset parameter based on the difference between the measurement baseline value and the global baseline reference.

10. The system according to claim 9, wherein the sensor measurement parameters, the global baseline reference, the threshold baseline value, and the previous baseline value are received from a database.

11. The system of claim 10, wherein the operations further comprising updating the previous baseline value in the database by setting the previous baseline value to the measurement baseline value.

12. The system of claim 8, wherein determining the offset parameter comprises:
- determining that the measurement baseline value is above a threshold baseline value; and
- determining the offset parameter based on the difference between the previous baseline value and the global baseline reference.

13. A computer program product comprising a non-transitory machine-readable medium storing instructions that, when executed by at least one programmable processor that comprises at least one physical core and a plurality of logical cores, cause the at least one programmable processor to perform operations comprising:
- receiving, from a methane detection system comprising a sensor, data characterizing methane detection by the sensor and sensor measurement parameters, wherein the data characterizing methane detection comprises a plurality of methane measurements and detection times associated with the plurality of methane measurements; wherein the sensor is located at an industrial site;
- determining a first plurality of calibrated methane measurements by at least calibrating the plurality of methane measurements based on the sensor measurement parameters and one or more of a humidity and a temperature associated with the sensor;
- calculating an offset parameter based on a difference between a global baseline reference and one of a previous baseline value and a measurement baseline value associated with the first plurality of calibrated methane measurements; and
- providing a second plurality of calibrated methane measurements by at least subtracting the offset parameter from the first plurality of calibrated methane measurements.

14. The computer program product of claim 13, wherein the operations further comprising determining the measurement baseline value, the determining comprising:
- selecting a subset of calibrated methane measurements from the first plurality of calibrated methane measurements, wherein values of the subset of calibrated methane measurements are below a predetermined percentile value,
  wherein the measurement baseline value is a mean of the subset of calibrated methane measurements.

15. The computer program product of claim 14, wherein determining the offset parameter comprises:
- determining that the measurement baseline value is less than a threshold baseline value; and
- determining the offset parameter based on the difference between the measurement baseline value and the global baseline reference.

16. The computer program product according to claim 15, wherein the sensor measurement parameters, the global baseline reference, the threshold baseline value, and the previous baseline value are received from a database.

17. The computer program product of claim 16, wherein the operations further comprising updating the previous baseline value in the database by setting the previous baseline value to the measurement baseline value.

18. The computer program product of claim 14, wherein determining the offset parameter comprises:
- determining that the measurement baseline value is above a threshold baseline value; and
- determining the offset parameter based on the difference between the previous baseline value and the global baseline reference.

* * * * *